(12) United States Patent
Sijbers et al.

(10) Patent No.: US 9,996,951 B2
(45) Date of Patent: Jun. 12, 2018

(54) COMPUTERIZED TOMOGRAPHIC IMAGE EXPOSURE AND RECONSTRUCTION METHOD

(71) Applicants: Agfa HealthCare, Mortsel (BE); Universiteit Antwerpen, Antwerpen (BE)

(72) Inventors: Jan Sijbers, Mortsel (BE); Jeroen Cant, Mortsel (BE)

(73) Assignees: Agfa HealthCare, Mortsel (BE); Universiteit Antwerpen, Antwerpen (BE)

(*) Notice: Subject to any disclaimer, the term of this patent is extended or adjusted under 35 U.S.C. 154(b) by 27 days.

(21) Appl. No.: 15/310,216

(22) PCT Filed: May 6, 2015

(86) PCT No.: PCT/EP2015/059956
§ 371 (c)(1),
(2) Date: Nov. 10, 2016

(87) PCT Pub. No.: WO2015/173088
PCT Pub. Date: Nov. 19, 2015

(65) Prior Publication Data
US 2017/0221232 A1    Aug. 3, 2017

(30) Foreign Application Priority Data

May 12, 2014  (EP) .................................... 14167902

(51) Int. Cl.
*G06K 9/00*     (2006.01)
*G06T 11/00*    (2006.01)
(Continued)

(52) U.S. Cl.
CPC ........... *G06T 11/006* (2013.01); *A61B 6/5258* (2013.01); *G01N 23/046* (2013.01);
(Continued)

(58) Field of Classification Search
CPC ................................. A61B 6/00; G06T 11/00
(Continued)

(56) References Cited

U.S. PATENT DOCUMENTS 6,965,661 B2 * 11/2005 Kojima ................. G01T 1/1648
378/10
7,356,113 B2 * 4/2008 Wu ........................ A61B 6/025
378/22

OTHER PUBLICATIONS

Official Communication issued in International Patent Application No. PCT/EP2015/059956, dated Jul. 20, 2015.
(Continued)

*Primary Examiner* — Abolfazl Tabatabai
(74) *Attorney, Agent, or Firm* — Keating and Bennett, LLP

(57) ABSTRACT

A computerized tomographic image exposure and reconstruction method wherein an object is subjected to irradiation during a relative movement of a source of radiation, the object, and a radiation detector and wherein a digital representation of the radiation image of the object is computed by applying a tomographic reconstruction algorithm to image data read out of the irradiated radiation detector. A number of projection images are generated, each of the projection images being generated by integrating X-ray beams continuously emitted during the relative movement through a predefined movement path, and the created projection images are modeled in a tomographic reconstruction algorithm.

13 Claims, 4 Drawing Sheets

(51) Int. Cl.
  *A61B 6/00* (2006.01)
  *G01N 23/04* (2018.01)
(52) U.S. Cl.
  CPC ... *G06T 2211/412* (2013.01); *G06T 2211/416* (2013.01); *G06T 2211/424* (2013.01)
(58) Field of Classification Search
  USPC ....... 382/128, 129, 130, 131, 132, 133, 134; 378/4, 8, 21–27, 901; 600/407, 410, 411, 600/425, 427
  See application file for complete search history.

(56) References Cited

OTHER PUBLICATIONS

Michielsen et al., "Patchwork reconstruction with resolution modeling for digital breast tomosynthesis", Medical Physics, AIP, vol. 40, No. 3, Feb. 28, 2013, pp. 031105-1-031105-10.
Kingston et al., "Mapping Between Digital and Continuous Projections via the Discrete Radon Transform in Fourier Space", Proc. VIIth Digital Image Computing: Techniques and Applications, Dec. 10-12, 2003, pp. 263-272.

\* cited by examiner

COMPUTERIZED TOMOGRAPHIC IMAGE EXPOSURE AND RECONSTRUCTION METHOD

CROSS REFERENCE TO RELATED APPLICATIONS

This application is a 371 National Stage Application of PCT/EP2015/059956, filed May 6, 2015. This application claims the benefit of European Application No. 14167902.7, filed May 12, 2014, which is incorporated by reference herein in its entirety.

BACKGROUND OF THE INVENTION

1. Field of the Invention

The present invention relates to a computerized method for tomographic image exposure and reconstruction.

2. Description of the Related Art

Computed tomography involves a first step of acquiring X-ray projection images (also called X-ray projections) by irradiating a patient or an object with an X-ray beam emitted in different directions and detecting the X-ray projection images by means of a radiation detector and generating a digital representation of these projection images.

A 3D image of the patient is then computed by applying a tomographic reconstruction algorithm to the acquired digital X-ray projection images.

The multitude of X-ray projection images that are required for tomographic image reconstruction can be acquired in different ways.

In a first method referred to as step-and-shoot protocol, an X-ray tube and radiation detector are stationary and move to a next location only in between exposures. While this protocol is the easiest from an image reconstruction point of view, it poses severe constraints on the design of the modality and typically leads to longer acquisition times.

An alternative acquisition strategy is to keep the X-ray source in a constant motion, the so called continuous acquisition mode. When conventional reconstruction algorithms are applied, the inherent angular integration of the beams during exposure causes blurring in the reconstructed images. Typically, this is considered an unwanted side effect of this acquisition mode and therefore the acquisition protocol is designed to limit the angular beam integration as much as possible. In a spiral CT scanner for example, the constant motion of the X-ray tube and the table enables a heavily reduced acquisition time compared to the original step-and-shoot modality, while a high number of projections reduces the angle of integration and limits the blurring in the reconstructed images.

In more recent tomosynthesis and cone-beam CT systems, a flat panel detector is used to capture the X-rays. Compared to CT scanners, these detectors are typically slower and acquisitions are made with a flashing X-ray source, which rotates slowly and radiates the subject at specified intervals. The constantly moving tube in continuous acquisition mode also allows a shorter acquisition time, at the cost of a slightly reduced resolution with step-and-shoot reconstruction algorithms, caused by the angular integration of the beams during the X-ray flashes. The angle of integration during a projection is limited by a short exposure time and low rotation speed.

It is an object of this invention to improve the reconstruction image quality.

In the publication by Michielsen Koen et al: "Patchwork reconstruction with resolution modeling for digital breast tomosynthesis", Medical Physics, AIP, Melville, N.Y., US, vol. 40, no. 3, a computerized tomographic image exposure and reconstruction method is disclosed wherein an object is subjected to irradiation during a relative movement of a source of radiation, said object and a radiation detector and wherein a digital representation of the radiation image of said object is computed by applying a tomographic reconstruction algorithm to image data read out of the irradiated radiation detector. A number of projection images are generated and are modeled into a tomographic reconstruction algorithm.

SUMMARY OF THE INVENTION

Preferred embodiments of the invention provide a tomographic image acquisition and reconstruction method based on continuous exposure during acquisition of each of the projection images as set out below.

Other preferred embodiments of the invention are also set out below.

According to a preferred embodiment of the invention a continuous acquisition model is considered whereby each projection image is obtained by subjecting an object to irradiation during a relative movement of a source of radiation, the object and a radiation detector. The relative movement in is a continuous movement over a pre-defined movement path.

Projection images are acquired by integrating X-ray beams emitted by the source of radiation from different positions on a pre-defined movement path. The irradiation is thus also continuous within said pre-defined movement path, e.g. a circular or linear path.

The continuous projections are modeled in a tomographic reconstruction algorithm, such as Simultaneous Iterative Reconstruction Technique (SIRT) or Filter-Backprojection Algorithm (FBP).

X-ray projection images are detected by a radiation detector which is in one preferred embodiment a two-dimensional flat panel direct radiography detector arranged to capture the continuous projections.

Alternative detector types such as line detectors are also possible.

Each line of such a flat panel direct radiography detector is read out consecutively and the movement path of the relative movement during the irradiation of this line is taken into account when the continuous projections acquired in a line are applied in the reconstruction algorithm.

The continuous relative movement of source of radiation, object and radiation detector can be implemented in various ways adapted to the envisaged type of application.

In one example source of radiation and detector are rotated continuously around a stationary object. The rotation center of this movement is either fixed or can be moving itself, e.g. translating.

In another preferred embodiment the continuous relative movement is obtained by continuously rotating a source relative to a stationary detector or to a translating detector.

The relative movement of source and detector may be non-linear or non-circular.

In still another application the object is rotating and the source—detector set up is stationary.

The present invention has been developed with regard to X-ray irradiation of a patient.

The invention is also applicable to other types of radiation such as electron beam radiation, gamma rays etc.

It is applicable for examination of the human body but can also be applied for examination of other types of applications such as veterinary tomography or tomographic material examination.

The effect on the image quality of reconstructions modeling continuous exposures compared with reconstructions from a step-and-shoot model with equal total radiation dose and number of projections is an increased reconstruction image quality near the rotation center.

For specific applications such as region of interest tomography, reconstructions from continuous exposures may significantly improve the image quality relative to the step-and-shoot protocol. Acquisition speed can be increased compared to the step-and-shoot protocol and less streak artifacts appear in the reconstruction.

Further advantages and preferred embodiments of the present invention will become apparent from the following description and drawings.

DETAILED DESCRIPTION OF THE PREFERRED EMBODIMENTS

A preferred embodiment method of the present invention is applied in a tomographic radiation image recording system in which a relative movement is performed between a source of radiation, such as an X-ray source, and a radiation sensitive detector, preferably a 2 dimensional direct X-ray detector.

In a preferred embodiment of this invention, a continuous relative movement of the radiation detector, the source of radiation and an object is envisaged.

During this continuous relative movement, the irradiation is also continuous, i.e. the X-ray source continuously emits radiation.

The emitted radiation is attenuated by an object placed in the irradiation path.

Next the attenuated radiation is detected by the X-ray detector and the detector is read out so as to generate so-called digital projection images.

The digital projection images thus generated are applied to a computation module that computes the attenuation coefficients of the irradiated object, also called the image, by applying a tomographic reconstruction algorithm. Reconstruction algorithms are well-known in the art.

Streak artifacts are a common problem in few-projection reconstructions (taking into account a small number of projections)

Figure 2A:
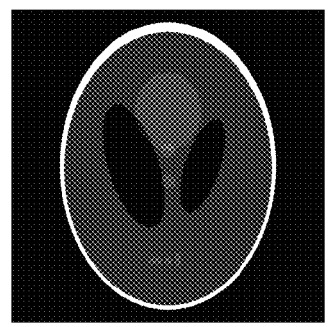
FIGS. 2(a) to 2(c) show a reconstruction of a Shepp Logan phantom (a) with sufficient (b) and with few view (c) projections, showing typical artefacts.
Figure 2B:
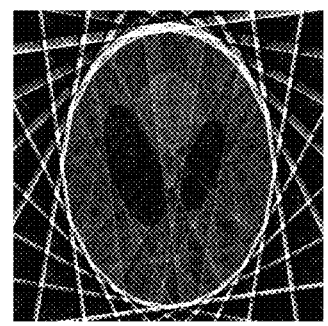
Figure 2C:
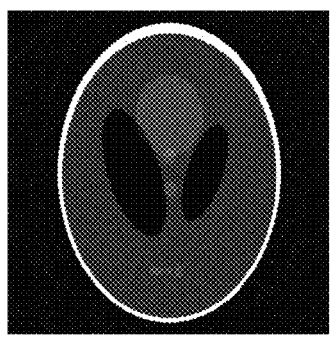

FIG. 2 illustrates the appearance of such streak artifacts.

For a parallel beam geometry, the rationale for creating continuous projections can be found in the central slice theorem. According to this theorem, the Fourier transform of a 1D projection of an image corresponds to a line in the Fourier transform of the image. A reconstruction from only a few projections therefore suffers from the well known streak artifacts, due to insufficient information about the Fourier space.

Figure 1A:
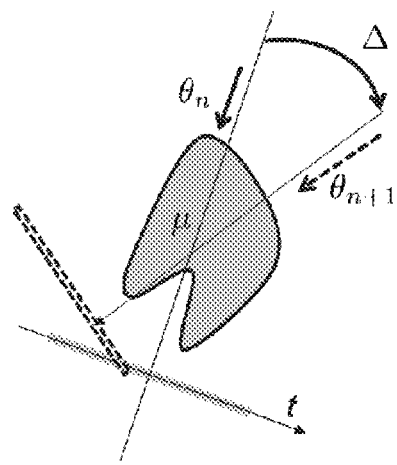
FIG. 1 (a) is a graphical illustration of an example parallel beam image acquisition geometry in two dimensions. Parallel beams are acquired at angles $\theta_n = n\Delta$ with $n=1, \ldots, N$ FIG. 1 (b) shows the corresponding lines of these projections in the Fourier space. In a continuous acquisition, the detector integrates all beams between $\theta_n$ and $\theta_{n+1}$ and and thus gathers information from the entire area in the Fourier space between the two angles of the static projections.

To illustrate this, an example acquisition geometry is shown in FIG. 1(a). Parallel beams are acquired at angles $\theta_n = n\Delta$ with $n=1, \ldots, N$ FIG. 1 (b) shows the corresponding lines of these projections in the Fourier space. In a continuous acquisition, the detector integrates all beams between $\theta_n$ and $\theta_{n+1}$ and and thus gathers information from the entire area in the Fourier space between the two angles of the static projections.

Conceptually, one can easily understand that by acquiring only a few projection images, the Fourier space of the image will be severely undersampled and hence the reconstructed image will contain reconstruction artifacts.

This can be seen in FIG. 2 (c), where the reconstruction from only 10 projections clearly shows the so called streak artifacts.

A preferred method of the present invention is based on continuous projections. As opposed to 'static' projections, 'continuous' projections are acquired by constantly moving X-ray source, object and detector relatively over a pre-defined path during acquisition of each of a series of projection images. During this movement the X-ray source is constantly irradiating the object.

FIG. 1a illustrates this concept for a two-dimensional parallel beam geometry. Where the 2 static projections represent 2 lines in the Fourier space (FIG. 1b), a continuous projection will integrate all rays between angles $\theta_n$ and $\theta_{n+1}$ and thus sample the entire area in the Fourier space between the two corresponding lines of the static projections.

The continuous projections are then modeled into a reconstruction algorithm such as the well-known SIRT algorithm or the FBP algorithm.

This modeling is explained starting from a step-and-shoot protocol which is not part of this invention. The paragraphs below explain the modeling for a parallel beam geometry with a stationary object and a source-detector system that rotates on a circular path around the object, but can be easily generalized to other geometries and other relative motions of object, source and detector.

The attenuation of an X-ray beam in the case of a step-and-shoot protocol, further on called static projection, can be expressed as follows:

$$I_n^s(t) = I_o \exp\left(-\int_{L_{t,\theta_n}} \mu(x, y) ds\right) \quad (1)$$

with $(x,y)=(t\cos\theta_n-s\sin\theta_n, t\sin\theta_n+s\cos\theta_n)$ Furthermore, $I_0$ is the intensity measured by the detector without object and I the intensity after attenuation by the object. The attenuation coefficients of the imaged object are represented by $\mu(x,y)$, and the line integral is taken over the X-ray beam $L_{t,\theta_n}$ from source to detector as illustrated in FIG. 1(a).

After transformation of the projection data by a division by ln $$\ln\left(\frac{I_0}{I_n^s(t)}\right)$$

and discretization, Eq. (1) can be expressed as a linear combination of the attenuation coefficients in x along the path of the ray:

$$b_i = \sum_j a_{i,j} x_j \quad (2)$$

where b represents the projection data and $b_i$ the projection pixel at position i. The image vector x is the discrete representation of $\mu$, and the weight of the attenuation coefficient at image pixel $x_j$ is $\alpha_{i,j}$, which is related to the intersection length of the ray with this pixel.

The combination of Eq. (2) for all projection pixels leads to a system of linear equations $$b = Ax \quad (3)$$

where $A=\{\alpha_{i,j}\}$ represents the system matrix, x the vector of unknown attenuation coefficients in the discrete representation of $\mu$ and b the b the entire projection data.

In case of continuous projections, each projection value $I_n^c(t)$ is the result of the integration of photons during rotation of the source-detector system from $\theta_n$ to $\theta_{n+1}=\theta_n+\Delta$. When the same total radiation dose is administered and the X-ray source and detector move relatively with constant speed, the measured intensity is given by:

$$I_n^c(t) = \frac{I_0}{\Delta}\int_{\alpha=\theta_n}^{\theta_{n+1}} \exp\left(-\int_{L_{t,\alpha}} \mu(x,y)ds\right)d\alpha \quad (4)$$

with $(x,y)=(t\cos\alpha-s\sin\alpha, t\sin\alpha+s\cos\alpha)$

In Eq. (4), the tube is assumed to emit a constant density $I_0$.

To obtain a discrete formulation of Eq. (4), S rays are sampled between $\theta_n$ and $\theta_{n+1}$. Eq. (2) is modified to:

$$b_i = -\log\left(\frac{1}{S}\sum_{s=0}^{S-1} \exp\left(-\sum_j \alpha_{i,j,s} x_j\right)\right) \quad (5)$$

where $\alpha_{i,j,s}$, now represents the weight of the attenuation coefficient at pixel $x_j$ for the beam with angle $$\theta_n + \frac{s}{S}\Delta$$

Figure 1B:
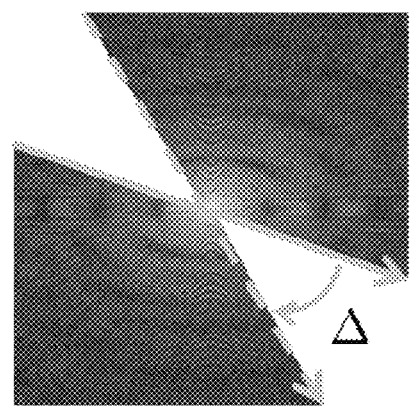

The sampling factor S should be chosen high enough to correctly sample the full area between the corresponding lines in the Fourier space as illustrated in FIG. 1b. The coefficients $\alpha_{i,j,s}$ can be obtained by modeling the sampled continuous projections system as a static projections system with S×N projections.

Reconstruction with Continuous SIRT

The system of equations (3) can be solved using the State of the art Simultaneous Iterative Reconstruction Technique (SIRT) algorithm, which can be written in matrix formulation as:

$$x^{(k+1)}=x^{(k)}+CA^TR(b-Ax^{(k)})$$

where $x^k$ represents the reconstructed image at iteration k and C and R the diagonal matrices with the inverse column and row sums of the system matrix A, respectively.

The operation $Ax^{(k)}$ corresponds to a so called forward projection, and the transpose $A^T$ is referred to as the backprojection operator.

With static exposures according to the prior art, this forward projection comes down to a weighted sum of image pixel values on a ray from source to detector, using an interpolation scheme between all pixels that are partially intersected by this ray. Similarly, the backprojection is a weighted redistribution of a value across the same image pixels in the neighbourhood of that ray.

Figure 4:
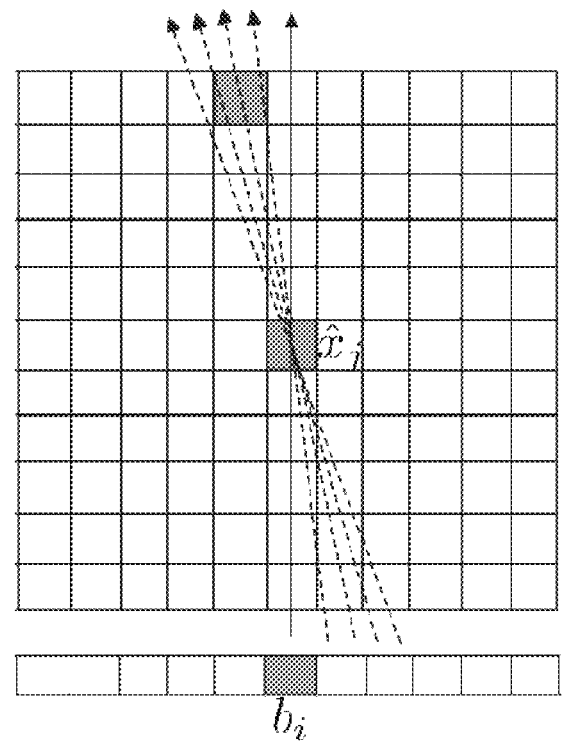
FIG. 4 illustrates the backprojection of a value $b_i$ along a single ray (full line) for a static exposure, and along a multiple of rays (full and dotted lines) for a continuous exposure.

For the protocol with continuous projections the forward and backward projectors are adapted. Instead of backprojecting a value along a single ray, this value is distributed along S rays corresponding to S source-detector positions of each exposure as illustrated in FIG. 4 for a parallel beam 2D geometry with static object and a source-detector system rotating along a circular path.

The forward projector is modeled by S rays matching the sampled continuous exposure.

Continuous Projections and Filter-Backprojection Algorithm (FBP)

In an alternative preferred embodiment the continuous projections are reconstructed with the Filter-Backprojection (FBP) Algorithm instead of the SIRT algorithm.

To this extent, a virtual static sinogram consisting of S×N lines is created from the N lines in the continuous sinogram by duplicating each line S times. More advanced upsampling techniques (sinogram interpolation techniques) could be used as well.

The virtual sinogram is then reconstructed by applying the FBP algorithm as if it originated from S×N different angles, equidistantly spread over the entire angular range. The benefit of using FBP over SIRT for reconstructing the continuous projections is an increased computation speed.

Line-By-Line Reconstruction

In a continuous projections system, the X-ray source, object and detector are in a constant relative motion while constantly emitting radiation. To ensure full angular coverage of the continuous projections, the detector should start integrating the X-rays for the next projection immediately after the end of the previous projection. Therefore the time needed for the detector to read out the signal should be as small as possible.

Figure 3:
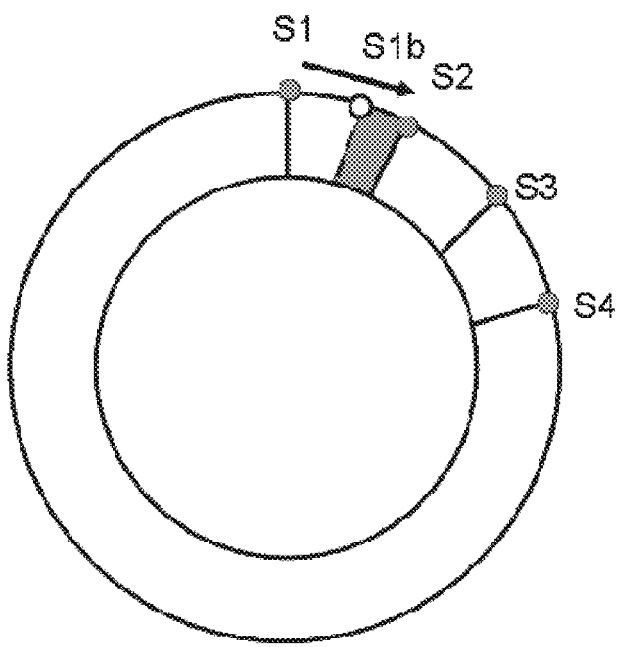
FIG. 3 illustrates the aspect of line by line readout of a detector. In this example, the X-ray source moves on a circular path around the object. The start positions of the different continuous exposures are indicated by S1, S2, etc. The start of the read out of the detector for the first continuous exposure is indicated by S1b and the end of this read-out by S2. As the source is continuously emitting X-rays and each detector line is read out consecutively, this illustrates that each detector image line is covered by a different angular range of radiation. This is modeled in the reconstruction algorithm.

In case of a (cone beam system using a) flat panel detector, the time needed for reading out a full image from the detector cannot be neglected, as illustrated in FIG. 3 for an example of a circular cone beam geometry. The starting points of the X-ray source for the acquisitions of the projection images are marked with S1, S2, . . . . If the X-ray source is continuously moving at a constant rotation speed, the flat panel detector readout occurs during the trajectory S1b-S2.

As the source is continuously emitting X-rays and each detector line is read out consecutively, this illustrates that each detector image line is covered by a different angular range of radiation. This is modeled in the reconstruction algorithm.

Line-by-line reading and resetting of the detector solves the read out delay. This causes each line to collect information from a slightly shifted angular range compared to its neighbouring lines, which can also be modeled in the reconstruction.

For example, during the time frame $t_d$ for reading out the detector, every line in the flat panel detector is read out and reset consecutively. With a constantly emitting source on a circular path and a time between two read outs of $t_d$, the actual angular end position of the X-ray source for a line at read out time depends on the projection index n and the row index r:

$$\theta_{n,r} = \theta_{n+1} + \frac{r-1}{R}\Delta$$

where R is the total number of lines in the detector. This can be modeled into the continuous reconstruction algorithm. The ray angles for the forward and backward projection not only depend on the projection image number, but also on the line number.

While the present invention has been described in connection with specific and/or preferred embodiments thereof, it will be understood that it is not intended to limit the invention to those preferred embodiments.

The invention claimed is:

1. A computerized tomographic image exposure and reconstruction method, the method comprising the steps of:
   subjecting an object to irradiation during a relative movement of a source of radiation, the object, and a radiation detector to obtain a radiation image;
   computing a digital representation of the radiation image of the object by applying a tomographic reconstruction algorithm to image data detected by the radiation detector; and
   generating a plurality of projection images by integrating X-ray beams continuously emitted during the relative movement through a predefined movement path; wherein
   the plurality of projection images are modeled in a tomographic reconstruction algorithm.

2. The method according to claim 1, wherein the radiation detector is a 2-dimensional flat panel detector arranged to capture the plurality of projection images.

3. The method according to claim 2, wherein lines of the 2-dimensional flat panel detector are read out consecutively; and a start position and an end position of the predefined movement path are taken into account when projections acquired in a line are reconstructed by the reconstruction algorithm.

4. The method according to claim 1, wherein the modeling of the plurality of projection images in the tomographic reconstruction algorithm is performed by:
   creating a projection geometry consisting of a set of intermediate projection positions for a continuous projection distributed over the predefined movement path; and
   duplicating a value of the continuous projection for each intermediate projection position in the set of intermediate projection positions in the reconstruction algorithm.

5. The method according to claim 4, wherein the reconstruction algorithm is an FBP algorithm implemented by applying the reconstruction algorithm to the duplicated continuous projections.

6. The method according to claim 1, wherein the reconstruction algorithm is an iterative reconstruction algorithm including:
   a forward tomographic projection obtained by combining the intermediate projection positions in the set of intermediate projection positions to create a forward continuous projection; and
   a back projection obtained by distributing a projection difference image along the predefined movement path of each intermediate projection position in the set of intermediate projection positions.

7. The method according to claim 1, wherein the relative movement is obtained by continuously rotating the source of radiation and the radiation detector around a fixed rotation center and the object is stationary.

8. The method according to claim 1, wherein the relative movement is obtained by continuously rotating the source of radiation and the radiation detector around a moving rotation center and the object is stationary.

9. The method according to claim 1, wherein the relative movement is obtained by continuously rotating the source of radiation relative to the radiation detector, and the radiation detector is stationary.

10. The method according to claim 1, wherein the relative movement is obtained by a continuously rotating the source of radiation and moving the radiation detector.

11. The method according to claim 1, wherein the relative movement of the radiation source and the radiation detector is non-linear.

12. The method according to claim 1, wherein the relative movement of the radiation source and the radiation detector is non-circular.

13. The method according to claim 1, wherein the object is rotating and a combination of the radiation source and the radiation detector is stationary.

* * * * *